United States Patent [19]

Eastman

[11] 4,371,730

[45] Feb. 1, 1983

[54] DEHYDROGENATION OF ORGANIC COMPOUNDS WITH A ZINC SILICATE CATALYST

[75] Inventor: Alan D. Eastman, Bartlesville, Okla.

[73] Assignee: Phillips Petroleum Company, Bartlesville, Okla.

[21] Appl. No.: 270,697

[22] Filed: Jun. 5, 1981

[51] Int. Cl.³ .................... C07C 5/333; C07C 5/367
[52] U.S. Cl. .................... 585/627; 585/379; 585/440; 585/442; 585/443; 585/654; 585/657; 585/658
[58] Field of Search ............... 585/379, 440, 442, 443, 585/657, 654, 658, 627

[56] References Cited

U.S. PATENT DOCUMENTS

| | | | |
|---|---|---|---|
| 2,221,301 | 11/1940 | Kipper | 585/654 X |
| 2,480,520 | 8/1949 | Thacker | 585/654 X |
| 2,608,534 | 8/1952 | Fleck | 585/654 X |
| 3,207,807 | 9/1965 | Bajars et al. | 260/680 |
| 3,211,800 | 10/1965 | Bajars | 260/680 |
| 4,176,140 | 11/1979 | Bertus et al. | 585/661 X |

*Primary Examiner*—Thomas A. Waltz

[57] ABSTRACT

The catalytic dehydrogenation of at least one dehydrogenatable organic compound which has at least one

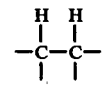

grouping is carried out in the presence of a zinc silicate catalyst and in the substantial absence of free oxygen.

10 Claims, No Drawings

DEHYDROGENATION OF ORGANIC COMPOUNDS WITH A ZINC SILICATE CATALYST

This invention relates to an improved catalytic process for the dehydrogenation of organic compounds.

Dehydrogenation processes for the conversion of organic compounds to compounds having a higher degree of unsaturation include both thermal noncatalytic processes and catalytic processes. The noncatalytic processes generally have undesirable side reactions, low order of conversion and yield and poor product selectivity. The catalytic processes are generally characterized by the particular catalytic material employed and the conditions under which the processes are operated, e.g., in the absence or presence of oxygen. While a number of such catalytic processes have achieved some measure of success, there is a continuing search to develop catalytic materials and processes which exhibit high activity, high yield of desired product, high selectivity to desired product, and longevity and which keep undesirable side reactions to a minimum. It is thus an object of this invention to provide an improved catalytic process for the dehydrogenation of organic compounds which provides at least some of the desired properties.

In accordance with the present invention, a dehydrogenatable organic compound is contacted with a zinc silicate catalyst in the substantial absence of free oxygen to convert the dehydrogenatable organic compound to compounds having a higher degree of unsaturation. The dehydrogenation process is preferably carried out in cycles consisting of a reaction period in which the dehydrogenatable organic compound is contacted with the zinc silicate catalyst and a regeneration period for the zinc silicate catalyst. During the regeneration period a free oxygen containing gas is passed in contact with the catalyst to regenerate the catalyst by burning off the carbonaceous material which may have formed on the catalyst.

Other objects and advantages of the invention will be apparent from the foregoing brief description of the invention and the appended claims as well as from the detailed description of the invention which follows.

The organic feedstocks which can be dehydrogenated in accordance with the present invention are dehydrogenatable organic compounds having from 2 to 12 carbon atoms per molecule and characterized by having at least one

grouping, i.e., adjacent carbon atoms, each having at least one hydrogen atom. Suitable compounds include paraffins, olefins, cycloaliphatics and alkyl aromatic compounds having from 2 to 12 carbon atoms per molecule. Particularly suitable are paraffins having from 2 to 5 carbon atoms per molecule and monoolefins having from 4 to 5 carbon atoms per molecule, branched or unbranched. Some examples of suitable hydrocarbon feedstocks are ethane, propane, butane, isobutane, pentane, isopentane, hexane, 2-methylhexane, n-octane, n-dodecane, 1-butene, 2-butene, 2-methyl-butene-1, 2-methyl-butene-2, 2-hexene, 1-octene, 3-methylnonene-4, 1-dodecene, cyclohexane, and the like and mixtures of any two or more thereof. Particularly appropriate is the conversion of ethane to ethylene, propane to propylene, butanes to butenes and butadiene, butenes to butadiene, and isopentane to isoamylenes and isoprene.

The dehydrogenation catalyst employed in the process of the present invention is a composition comprising zinc and silicon. Sufficient oxygen is present in the catalyst composition to satisfy the valence requirements of the zinc and silicon. Zinc and silicon are generally present as zinc silicate in the catalyst composition.

The zinc silicate catalyst composition may be prepared in any suitable manner. The zinc silicate is preferably prepared by intimately mixing suitable portions of zinc oxide and silica, preferably in a liquid such as water, and calcining the mixture at a temperature in the range of about 750° C. to about 1200° C. over time intervals ranging from about 1 hour to about 8 hours with the longer time intervals being used with the lower temperatures. Preferably, calcining temperatures in the range of about 900° C. to about 950° C. for time intervals in the range of about 2 to about 3 hours are used. The calcining can be accomplished in the presence of free oxygen or in an inert atmosphere but preferably the calcining is not carried out in a reducing atmosphere since the zinc metal produced by reduction of the zinc oxide is readily volatilized at the calcining temperature.

The silica used in preparing the zinc silicate preferably has a fine particle size to promote intimate mixing of the zinc oxide and silica. A flame hydrolyzed silica having a particle diameter less than one micrometer is particularly preferred. The atomic ratio of zinc to silicon can be any suitable ratio. The atomic ratio of zinc to silicon will generally lie in the range of about 1:1 to about 3:1 and will preferably lie in the range of about 1.7:1 to about 2.1:1 because the activity of the catalyst is greatest for atomic ratios of zinc to silicon in this range. The term "zinc silicate" is used regardless of the atomic ratio of zinc to silicon.

The dehydrogenation process of this invention can be carried out by means of any apparatus whereby there is achieved an alternate contact of the catalyst with the dehydrogenatable organic compound and thereafter of the catalyst with the oxygen-containing gaseous phase, the process being in no way limited to the use of a particular apparatus. The process of this invention can be carried out using a fixed catalyst bed, fluidized catalyst bed or moving catalyst bed. Presently preferred is a fixed catalyst bed.

In order to avoid any casual mixing of the organic compound and oxygen, provision is preferably made for terminating the flow of feed to the reactor and subsequently injecting an inert purging fluid such as nitrogen, carbon dioxide or steam. Any suitable purge time can be utilized. The purge duration will generally range from about 1 minute to about 10 minutes and will more preferably range from about 3 minutes to 6 minutes. Any suitable flow rate of the purge fluid may be utilized. Presently preferred is a purge fluid flow rate in the range of about 800 GHSV to about 1200 GHSV.

Any suitable dehydrogenation reaction time may be used in the dehydrogenation process. The dehydrogenation reaction time will generally be in the range of about 0.05 seconds to about 10 minutes and will preferably be in the range of about 0.1 to about 5 minutes.

Any suitable catalytic dehydrogenation temperature can be employed which provides the desired degree of catalytic activity in the dehydrogenation of the organic feedstock. The dehydrogenation temperature will generally be in the range of about 426° C. to about 705° and will more preferably be in the range of about 538° to about 677° C.

The catalytic dehydrogenation process can be carried out at any suitable pressure. The pressure of the dehydrogenation reaction will generally range from about 0.05 to about 250 psia.

Any suitable feed rate for the organic feedstock can be utilized. The organic feedstock feed rate will generally be in the range of about 50 to about 5,000 volumes of gaseous feedstock per volume of catalyst per hour and will preferably be in the range of about 100 to about 2500 volumes of gaseous feedstock per volume of catalyst per hour.

Any suitable time for the regeneration of the dehydrogenation catalyst can be utilized. The time for the regeneration of the dehydrogenation catalyst will generally range from about 1 to about 10 times the reaction period.

The regeneration effluent should be substantially free of carbon dioxide at the end of the regeneration period.

The amount of oxygen, from any source, supplied during the regeneration step will be at least the amount sufficient to remove substantially all carbonaceous materials from the catalyst. The regeneration step can be conducted at the same temperature and pressure recited for the dehydrogenation step although somewhat higher temperatures can be used, if desired.

The operating cycle for the dehydrogenation and regeneration process will generally include the successive steps of:

(1) Contacting a dehydrogenatable organic compound with the dehydrogenation catalyst;

(2) terminating the flow of the dehydrogenatable organic compound;

(3) optionally, purging the catalyst with an inert fluid;

(4) contacting the dehydrogenation catalyst with free oxygen;

(5) terminating the flow of the free oxygen; and (6) optionally, purging the catalyst with an inert fluid before repeating step (1).

The following example is presented in further illustration of the invention.

EXAMPLE

Catalyst Preparation

Zinc silicate having an atomic ratio of zinc:silicon=2.00 was prepared by combining 81.2 gms (1.00 moles) of powdered Mallinckrodt zinc oxide and 30.0 gms (0.50 moles) of Cab-O-Sil flame hydrolyzed silica in about 200 milliliters of water and mixing for 10 minutes in a Waring blender. The resulting slurry was dried in an oven at about 120° C. to remove water and then calcined in air for three hours at 815° C. After cooling, the resulting zinc silicate was crushed and screened and a −16+40 mesh fraction was obtained for testing.

A zinc oxide catalyst was prepared by mixing powdered Mallinckrodt zinc oxide with five weight percent of powdered polyethylene. The resulting mixture was compressed into tablets in a pelleting machine and the tablets were calcined for one hour in air at 538° C. The thus calcined tablets were crushed and screened and a −16+40 mesh fraction was obtained for testing.

Catalyst Test

The described catalysts were used to dehydrogenate ethane to ethylene and hydrogen. All runs were made at atmospheric pressure and 703° C. At these conditions, thermodynamic equilibrium for the reaction is about 43% ethane conversion. The procedure for both runs was as follows:

A one milliliter portion of the catalyst was placed in a quartz reactor and the quartz reactor was mounted vertically in a temperature controlled furnace. All fluids passed down-flow through the quartz reactor. Nitrogen flowed through the reactor continuously at 500 GHSV. After heating in air to 703° C., the catalyst was purged with nitrogen and then exposed to ethane during the process cycle. After completion of the process cycle, the catalyst was again purged with nitrogen and then regenerated with air. This sequence was then repeated. The gas hourly space velocity (GHSV) at standard temperature and pressure was 500 and 2500 for ethane and air respectively. One cycle consisted of one minute nitrogen, three minutes ethane, one minute nitrogen, and six minutes air.

Snap samples from the hydrocarbon stream were taken after 1, 2 and 3 minutes of the process cycle. The thus acquired snap samples were analyzed separately by gas-liquid chromatography. Averages of the analysis were used to determine ethane conversion and selectivity to ethylene. The results of the analysis are set forth in Table I.

TABLE I

| Catalyst | ZnO | Zn$_2$SiO$_4$ |
| --- | --- | --- |
| Weight, g | 1.590 | 0.637 |
| Cycle (% Conv./% sel.) | 1(17.7/90.6) | 1(48.0/96.0) |
|  | 315(14.7/96.6) | 315(14.4/95.8) |
|  | 451(15.4/94.5) | 451(9.4/95.0) |
|  | 575(12.9/96.2) | 575(5.9/93.0) |

Despite its much lower density, the zinc silicate possesses much higher initial activity than does the zinc oxide. Although the activity of zinc silicate decreases at a faster rate than zinc oxide, on comparable weight bases the zinc silicate is still more active than the zinc oxide after 575 process/regeneration cycles.

Reasonable variations and modifications are possible within the scope of the disclosure and the appended claims to the invention.

That which is claimed is:

1. A process for the catalytic dehydrogenation of at least one dehydrogenatable organic compound which has at least one

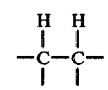

grouping comprising the step of contacting said at least one dehydrogenatable organic compound, under suitable dehydrogenation conditions in the substantial absence of free oxygen with a catalyst composition comprising zinc silicate.

2. A process in accordance with claim 1 wherein the atomic ratio of zinc to silicon in said catalyst composition is in the range of about 1:1 to about 3:1.

3. A process in accordance with claim 1 wherein the atomic ratio of zinc to silicon in said catalyst composition is in the range of about 1.7:1 to about 2.1:1.

4. A process in accordance with claim 1 wherein said dehydrogenatable organic compound is selected from the group consisting of paraffins having from 2 to 5 carbon atoms per molecule, monoolefins having from 4 to 5 carbon atoms per molecule, and mixtures of any two or more thereof.

5. A process in accordance with claim 1 wherein said suitable dehydrogenation conditions comprise a reaction period in the range of about 0.05 second to about 10 minutes, a dehydrogenatable organic compound feed rate in the range of about 50 to about 5,000 volumes of dehydrogenatable organic compound per volume of said catalyst composition per hour, a temperature within the range of about 426° C. to about 705° C., and a pressure within the range of about 0.05 psia to about 250 psia.

6. A process in accordance with claim 1 wherein said suitable dehydrogenation conditions comprise a reaction period in the range of about 0.1 second to about 5 minutes, a dehydrogenatable organic compound feed rate in the range of about 100 to about 2500 volumes of dehydrogenatable organic compound per volume of said catalyst composition per hour, a temperature within the range of about 538° C. to about 677° C., and a pressure within the range of about 0.05 psia to about 250 psia.

7. A process in accordance with claim 1 additionally comprising the steps of:
discontinuing the flow of said dehydrogenatable organic compound over said catalyst composition; and
contacting said catalyst composition, after the flow of said dehydrogenatable organic compound is discontinued, with a free oxygen-containing fluid under suitable regeneration conditions to thereby regenerate said catalyst composition.

8. A process in accordance with claim 7 wherein said suitable regeneration conditions comprise a regeneration period in the range of about 0.05 second to about 100 minutes, a feed rate of said free oxygen-containing fluid suitable to supply sufficient oxygen to remove substantially all of the carbon deposits from said catalyst composition, a temperature within the range of about 426° C. to about 705° C., and a pressure within the range of about 0.05 psia to about 250 psia.

9. A process in accordance with claim 7 additionally comprising the step of purging said catalyst composition with an inert fluid after the step of terminating the flow of said dehydrogenatable organic compound and before the step of regenerating said catalyst composition.

10. A process in accordance with claim 7 additionally comprising the steps of:
terminating the flow of said oxygen-containing fluid over said catalyst composition after said catalyst composition is substantially regenerated;
purging said catalyst composition with an inert fluid after the flow of said free oxygen-containing fluid is terminated;
terminating the flow of said inert fluid over said catalyst composition after said free oxygen-containing fluid is substantially purged from said catalyst composition; and
contacting the thus purged catalyst composition with said dehydrogenatable organic compound after the flow of said inert fluid is terminated.

* * * * *